United States Patent
Pelletier et al.

(12)

(10) Patent No.: US 6,350,237 B1
(45) Date of Patent: Feb. 26, 2002

(54) METHOD AND APPARATUS FOR MONITORING FETAL STATUS DATA

(75) Inventors: Andrew Michael Pelletier, Killingworth, CT (US); Lewis Bradford Knecht, Olney, MD (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/434,244

(22) Filed: Nov. 5, 1999

(51) Int. Cl.[7] .............................................. A61B 5/0444
(52) U.S. Cl. ....................................... 600/300; 600/511
(58) Field of Search ................................ 600/300, 453, 600/511; 128/970

(56) References Cited

U.S. PATENT DOCUMENTS 5,715,823 A    2/1998   Wood et al. ............ 128/660.01

FOREIGN PATENT DOCUMENTS

WO      WO 93/18710      9/1993

*Primary Examiner*—William E. Kamm
(74) *Attorney, Agent, or Firm*—Fletcher, Yoder & Van Someren

(57) ABSTRACT

A system is provided for remotely monitoring fetal status parameters. Status parameters are sampled from patient sensors and are processed and stored in a medical facility data management system. A general purpose data presentation application, such as a browser, is employed on a client side to access the data via a network, such as the Internet. Support software is called upon to format user-viewable pages and to insert data transmitted from the medical facility for remote viewing. The technique is particularly well suited to monitoring of a variety of parameters at various sampling rates for remote medical evaluation, such as in obstetrics applications.

7 Claims, 4 Drawing Sheets

METHOD AND APPARATUS FOR MONITORING FETAL STATUS DATA

FIELD OF THE INVENTION

The present invention relates generally to the field of systems for remotely monitoring fetal status. More particularly, the invention relates to a technique for accessing and viewing data presentations, such as graphical data charts, based upon patient monitoring in a client-server environment through the use of a server and browser, or similar arrangement.

BACKGROUND OF THE INVENTION

A wide variety of equipment and systems have been developed for monitoring the status of medical patients and procedures, particularly of a fetus and mother. In its simplest form, a patient monitoring system may consist of a sensing and monitoring apparatus located at the patient's bedside. Physicians, nurses and clinicians may thus maintain constant or periodic records, typically in real time, of the patient's condition. Monitors of this type include cardiac monitors, respiratory monitors, blood pressure monitors, chemical monitors, such as for oxygen take up, and so forth. In specific instances, such monitors are particularly key to determining the patient's condition and projecting immediate or medium-term medical needs. For example, in the field of obstetrics, patient condition parameters, such as fetal heartbeat, intensity and duration of contractions, and so forth, are commonly monitored to determine levels of fetal and maternal stress. Based upon such determinations, medications may be administered or modulated, or in certain instances, physician intervention may be warranted.

Continuous or periodic patient monitoring performs at least two roles. Firstly, the monitor provides extremely valuable feedback to care providers for evaluating the patient's condition and the need for medical attention. Moreover, where the devices are designed to maintain historical information, accurate records may be created for later review and analysis. Currently, such records may take the form of both electronic data, as well as hard copy, such as strip-chart records, and reports, and the like.

Significant changes in the manner in which care providers attend to patients have posed a series of challenges to conventional methods for monitoring patient status and providing information regarding this status. For example, highly specialized physicians may attend to a number of patients in various locations and institutions. Flexible organizations of this type have become extremely useful in offering high quality medical care almost independent of the location of either the patient, the institution, or the physician. While various systems have been developed to convey patient condition data to physicians and specialists, further improvement is still needed.

Depending upon the field of specialization, dedicated systems have been developed, along with specialized software, enabling care providers to obtain patient status information remotely. In one type of system, highly specialized monitoring and communications devices and software may be accessed by physicians via a network. The physician, however, must have access to a specialized work station, or at least to a compatible work station running software specifically designed to interface with that of the monitoring system. While arrangements of this type enable a degree of flexibility by allowing physicians to access the monitored information, they nevertheless impose significant constraints due to the specialized nature of the software and protocols used on both the monitoring side and on the physician or access side. Similar limitations may also be imposed by the existence of various versions of the monitoring or access software.

Where constraints of this type are imposed on either the medical institution or on the remote attending physician, the ultimate utility of the remote monitoring arrangement may be seriously jeopardized. Where an obstetrician is prevented or detained from obtaining up-to-date information on the status of a patient, for example, the physician's ability to order treatment from a remote location becomes more difficult and uncertain, and less timely. At present, no universal or generally widely accessible system has been developed for monitoring or delivering patient status data to avoid these drawbacks.

There is a need, therefore, for an improved technique for monitoring patient status remotely. There is, at present, a particular need for a technique which avoids the need for specialized software, updated and compatible versions, and thus delays in transmitting, translating, and displaying data.

SUMMARY OF THE INVENTION

The present invention provides a technique for remote fetal monitoring designed to respond to these needs. The system is particularly well suited to remote monitoring of patients in medical institutions by physicians equipped with general purpose computers or even laptop, hand held or portable computers. The technique may, however, be extended to various monitoring situations, including emergency medical situations, such as those in which monitoring equipment is located in mobile work stations, such as ambulances. In a particular form of the device, obstetric patient parameters are monitored, including fetal heartbeat and uterine contractions. The technique is ideal for maintaining both electronic and hard-copy records, as well as for transmitting such historical information and real-time updated information to any remote location accessible via a network, such as the Internet.

In a presently preferred configuration, the technique is implemented in a client-server environment. Monitoring equipment at the patient location encodes the patient parameters of interest. The monitoring equipment is coupled to a computer system which includes a server for storing and transmitting data to a remote location upon demand. On the client side, a work station, which may be stationary or mobile, is equipped with a general-purpose browser or a similar network interface. The data is incorporated into a presentation page which is viewable on the browser. Such presentation pages may be configured, for example, through the use of a mark-up language. By employing a generally standard user interface, the constraints imposed on the system from a specialization and compatibility standpoint are resolved minimized, or avoided. Moreover, data may be simply and efficiently updated and transmitted in small packets to provide the most recent patient data available. Any significant changes to the monitoring or data processing hardware or software may be performed on the server-side without requiring updating of client-side software.

DETAILED DESCRIPTION OF THE INVENTION

Figure 1:
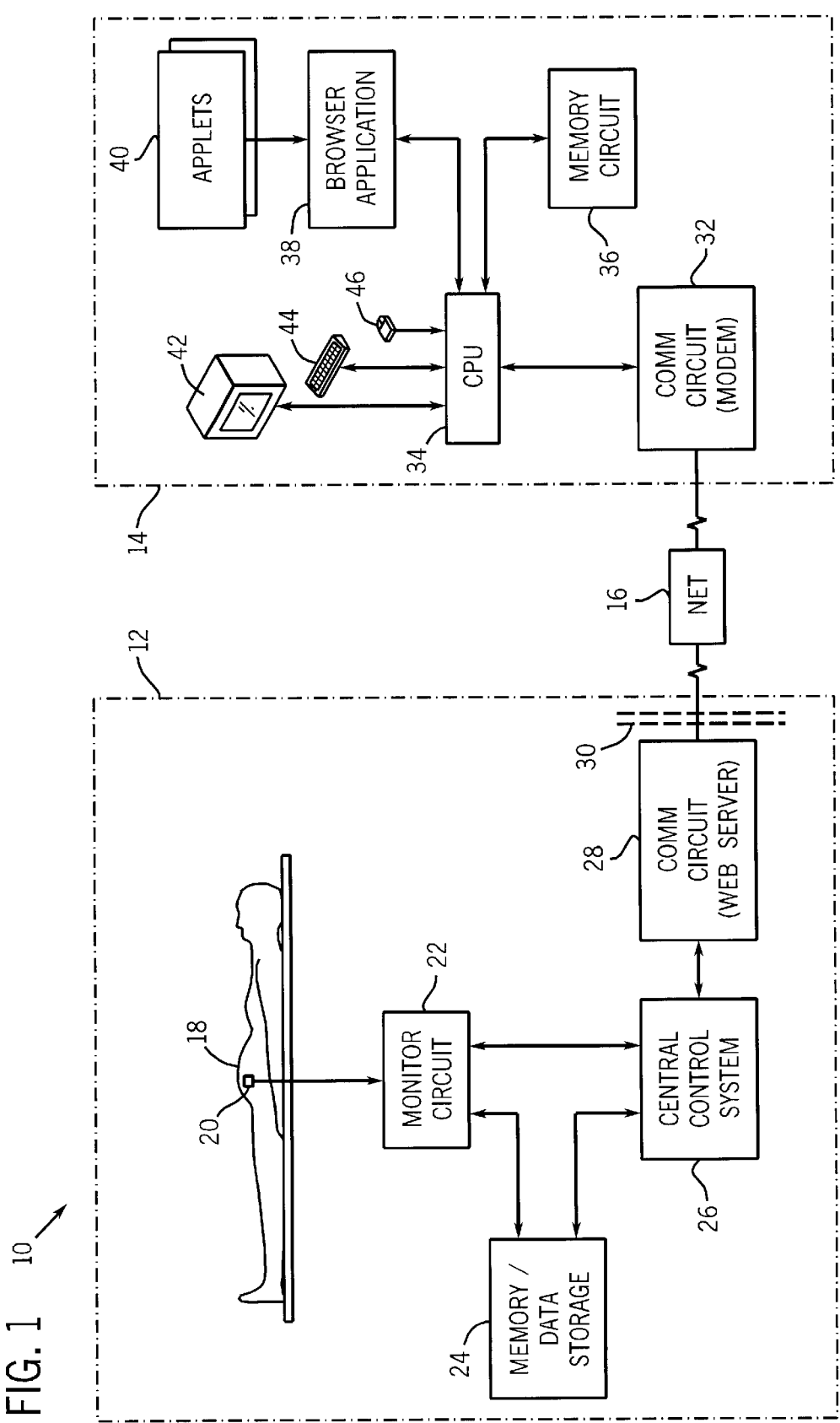
FIG. 1 is a diagrammatical overview of a remote fetal monitoring system in accordance with certain aspects of the present technique.

Turning now to the drawings, and referring first to FIG. 1, a fetal monitoring system 10 is illustrated as including a medical service facility 12 and a remote monitoring station 14. It should be noted that, in general, medical service facility 12 may include one or more institutional locations, such as a hospital, clinic, or the like. Medical service facility 12 may also include various mobile stations, such as ambulances, mobile clinics, and so forth. Similarly, remote monitoring station 14 may include components based at a specific location, such as a clinical office or residence. However, station 14 may likewise be mobile, such as including the components described below, configured in a portable or laptop computer system.

Medical service facility 12 and remote monitoring station 14 are designed to be linked to one another to exchange data via a network as indicated generally at reference numeral 16. While any suitable network may be used, in the presently preferred configuration, network 16 includes an open network, such as the Internet. Other suitable networks may include virtual private networks, dedicated or proprietary networks, and so forth. While the network link between the facility and the remote monitoring station may be permanent, in the presently preferred configuration, the network link is established at will, such as via conventional telephony lines and protocols.

Medical service facility 12 includes circuitry and systems for monitoring the physiological condition of a patient 18. In the illustrated embodiment, the monitoring circuitry is specifically designed to obtain obstetric data including fetal heartbeat rate and data indicative of uterine activity, as a basis for identifying timing and intensity of uterine contractions. In the diagrammatical view of FIG. 1, a sensor 20 is placed on patient 18 and samples heartbeats of a fetus at a frequency of approximately 1 kHz. Sensor 20 may also include an intrauterine catheter or an exterior sensor for detecting muscle contractions or pressure corresponding to contractions. In general, however, sensor 20 may include any suitable transducer or transducers adapted to encode signals corresponding to parameters of interest in evaluating the patient's condition.

Signals from sensor 20 are conveyed to a microprocessor-based monitoring circuit 22. Monitoring circuit 22 may perform various signal processing functions, including signal filtering, noise reduction, and so forth. In particular, for high frequency fetal heartbeat rate sensing, monitoring circuit 22 may analyze sampled data to determine timing of heartbeats for later storage and analysis. It should be noted that the various sensors utilized in the present technique need not be of the same type or operate on similar sampling frequencies. Thus, a fetal heartbeat rate monitor may sample at a higher frequency than a sensor designed to monitor uterine activity. In either case, monitoring circuit 22 may process the sensed signals differently depending upon the nature of the sensor and of the data obtained.

Monitoring circuit 22 is coupled to a memory and data storage circuit 24, and to a central control system 26. As noted above, certain of the subcomponents of facility 12, including memory and data storage circuit 24 and central control system 26 may be operated locally with respect to monitoring circuit 22 or at diverse locations. For example, in a large medical complex, monitoring circuit 22 may be coupled to a central or dedicated memory and data storage system within the facility. Similarly, central control system 26 may be positioned locally with respect to monitoring circuit 22, or may include diverse components arranged to form the overall informatics system of facility 12. Control system 26 may typically include, for example, one or more personal computers, mainframe computers, work stations, servers, call routers, and so forth. Moreover, such equipment may be linked via a network, such as an intranet, to form the overall control system capable of carrying out the functions described herein, as well as other data management operations.

Control system 26 is coupled to communications circuitry as represented generally at reference numeral 28. Communications circuitry 28 will typically include a web server and any specialized router, modems, and support hardware and software for receiving network communications, routing the communications, and transmitting and receiving data as described below. In the embodiment illustrated in FIG. 1, facility 12 further includes security features, such as a firewall 30, which may be of any suitable design and configuration, for protecting data and the internal network within facility 12 from unwanted intrusion. In the preferred embodiment, certain additional screening functions are performed by control system 26 to provide controlled access to patient and other information as described below.

Remote monitoring station 14 is designed to receive user commands, to access information from medical service facility 12, and to display certain data transmitted from the facility as needed. In particular, station 14, which may be a personal, laptop or other general purpose computer, includes communications circuitry, designated generally by reference numeral 32, for coupling the remote monitoring station to the medical service facility via network 16. Communications circuitry 32 may include any suitable hardware and software, such as a standard modem and network software for addressing desired network sites, and for transmitting data to and from such sites. Communications circuitry 32 is coupled to a central processing unit 34 which may include any suitable processor, typically a microprocessor-based circuit. CPU 34 commands operation of the various components of station 14 to perform the functions described herein, as well as auxiliary functions such as those performed on computer work stations and portable computers. Where desired, CPU 34 may, of course, have limited capabilities, such as those provided in application-specific computer systems, palm-type computers, and the like. Memory circuitry 36 is coupled to CPU 34 and may include both volatile and non-volatile memory circuits, hard disc drives, tape drives, and so forth. Memory circuit 36 serves both to store application software needed by CPU 34, as well as configuration parameters, network settings, and downloaded data.

While specialized applications may be stored and executed by remote monitoring station 14, in the preferred embodiment, the monitoring station is provided with a general-purpose browser application, as represented at reference numeral 38. The browser application permits the user of monitoring station 14 to receive and view data from remote locations including medical service facility 12. The browser may be of any suitable type, such as browsers available from Netscape Communications Corporation under the designation Netscape® Navigator, or from Microsoft Corporation under the designation Internet Explorer. Such data presentations may be configured through various software applications and languages, particularly via markup languages including HTML, XML, and so forth. Specific applets 40 are also included in remote monitoring station 14 and are called upon as needed to support the display and data presentation functions implemented via browser application 38 as described more fully below. In particular, Java applets may be provided and called upon for defining specific data presentation configurations needed to format and display user-viewable pages within the remote monitoring station.

Station 14 may further include a series of input and output devices for receiving user configuration settings and commands, and for displaying data presentations upon demand. In the illustrated embodiment, for example, station 14 includes a monitor 42, a keyboard 44, and a mouse 46. Of course, these and other input and output devices may be included in the system depending upon the user needs. Other such devices may include printers, recorders, user-viewable alarms or monitors, and so forth.

Medical service facility 12 and remote monitoring station 14 may communicate with one another via any of a range of suitable protocols. For example, in a presently preferred configuration, data is exchanged in accordance with the Internet Protocol (IP), and the Transmission Control Protocol (TCP). The data monitored remotely may be formatted in pages which are viewed by the user via station 14. It should be noted that, as used herein, the term "page" includes a user interface display or similar arrangement which can be viewed by a user of the remote monitoring station, such as screens providing graphical or textual representations of data, messages, reports, and so forth. Moreover, as mentioned above, such pages may be defined by a markup language or programming language such as Java, Perl, Java script, or any other suitable language. The two-way data exchange between the medical service facility and the remote monitoring station, and the use of general-purpose data presentation applications, greatly facilitates the data exchange, minimizing the need for highly specialized software at the client side of the system. In a presently favored data flow, a presentation page or pages may be predefined and data, both historical and updated in real time, transmitted for viewing in a very efficient manner from both bandwidth and computational points of view.

Figure 2:
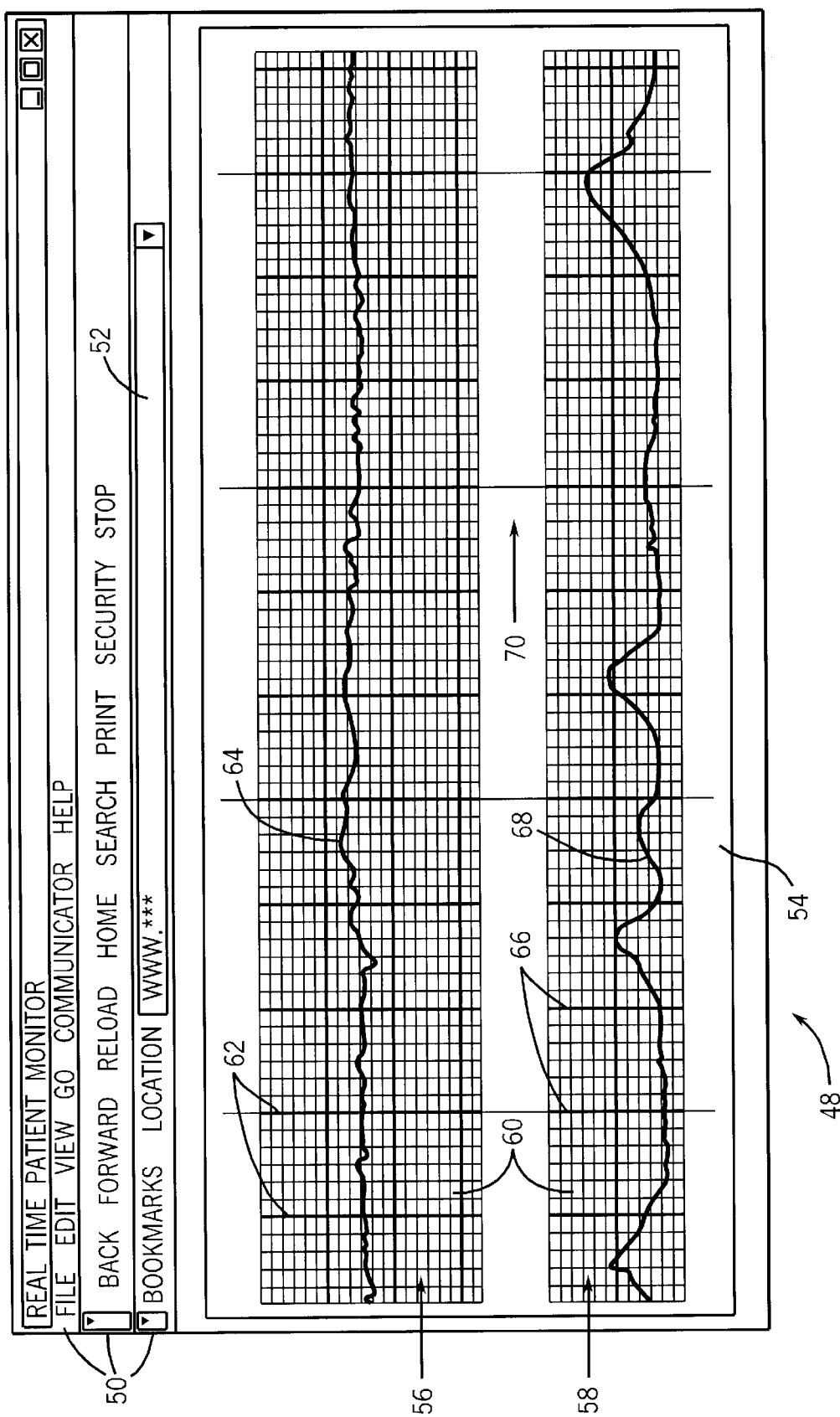
FIG. 2 is an exemplary graphical representation of fetal status data as it might appear on a general-purpose browser on the client side of the system of FIG. 1.

FIG. 2 is an exemplary portion of a web page data presentation of the type which may be transmitted between the medical service facility 12 and the remote monitoring station 14. As will be recognized by those skilled in the art, the data display 48 may be part of a page defined for a general-purpose web browser, such as a browser used for displaying Internet-distributed data. It should be noted, however, that such data presentation applications may also be used for a wide range of sources, including virtual private networks, intranets, dedicated networks, locally stored data, and so forth.

The data display 48 includes both features for navigating to desired sources of patient status data, as well as features for displaying the data in textual form, or as represented in FIG. 2, graphical formats. The display may thus include a series of interface menus 50 for locating desired presentations, storing presentations, or manipulating the presentations in various manners. In the illustrated embodiment, an address block 52 is provided for user input of network locations, typically in the form of uniform resource locator designations (URL's). Other types of address designations may, of course, be employed.

A display area 54 is provided in data display 48 for presentation of the patient status data of interest. Data relating to one or more patient status parameters may be provided, two such parameter data sets being displayed in FIG. 2. In the particular embodiment illustrated, both data presentations 56 and 58 are provided in the form of graphical displays emulating strip chart recorder output. In the particular embodiment illustrated in FIG. 2, a first data presentation 56 represents fetal heartbeat rates over time, while a second data presentation 58 represents uterine activity as an indication of maternal contractions for similar time periods. In the graphical representations, grids 60 are preferably provided to allow the user readily to distinguish both data levels and time periods. A series of vertical grid lines 62 in data presentation 56 provide an indication of time scales, with smaller grid lines representing 10 second subdivisions and bold lines representing minutes in the illustrated example. Vertically, a data trace 64 provides an indication of the level of the monitored parameter, in this case fetal heartbeat rate.

Other data presentations, such as presentation 58, may be displayed in the same or different units. In the illustrated embodiment, grid lines 66 of presentation 58 are on the same time scale and are in registration with those of data presentation 56. A second parameter trace 68 is provided in the second presentation, in this case representative of uterine activity or muscle contractions. Those skilled in the art will recognize that the registration of data in the various presentations may be particularly useful for identifying the cause and effect relationships between various patient condition variables, or between co-variables. In the illustrated embodiment, for example, a physician monitoring the information remotely may, at a glance, determine potential fetal stress resulting from maternal contractions.

The data presentations provided in display 48 may assume various forms and bases of progression. For example, in the embodiment illustrated in FIG. 2, the graphical traces are provided over time, as indicated by reference numeral 70. As noted above, the data populating the display may, however, be based upon a wide range of sampling rates. For example, in one presently favored embodiment, a fetal heartbeat trace 64 may be based upon feedback from a sensor sampling at approximately 1 kHz, while contraction data may be based upon sampling at a much lower rate, such as 1–4 Hz.

Figure 3:
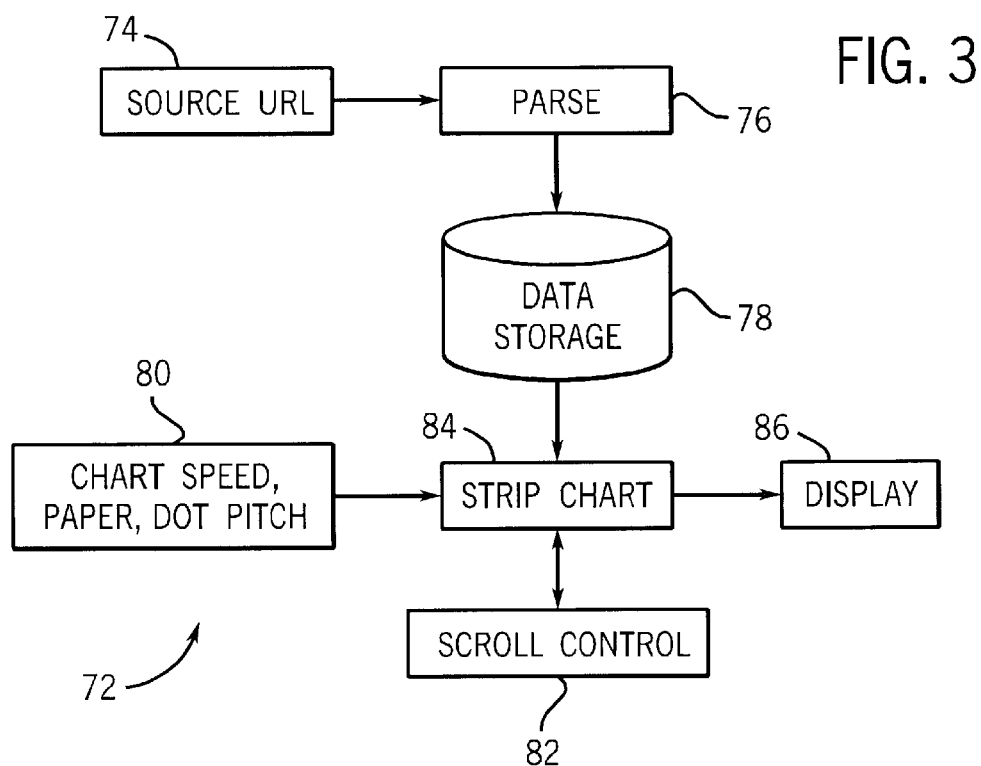
FIG. 3 is a data flow diagram illustrating the storage and formatting of data transmitted to the client system for presentation.

The data presentation available to the user of station 14 may be defined in various manners, particularly depending upon the type of data presented, the most useful or convenient form of presentation, the amount of data to be transmitted, and so forth. In a presently preferred configuration, various applets are called upon by browser application 38 (see FIG. 1) to define the presentation and to incorporate the transmitted data therein. FIG. 3 represents a data flow diagram for definition of the fetal monitor strip chart display illustrated in FIG. 2. The data flow, represented generally by reference numeral 72, begins with data obtained from the source URL as shown at reference numeral 74. This data will typically include numerical information defining various data points for formatting and presentation in display 48. In the present embodiment, the source URL data is obtained from communications circuitry 28 of facility 12 as illustrated in FIG. 1. The facility server passes an appropriate URL into the applet running on station 14. The applet then opens the URL, parses the data, as represented at reference numeral 76 in FIG. 3, and stores the data locally as represented at reference numeral 78. The server may further specify an encrypted hypertext transfer protocol connection (https), with the browser application at the monitoring station handling necessary decryption. Data storage at the monitoring station may be limited in time or in volume, with a typical fetal monitor strip chart display being limited to a maximum of four hours in the illustrated embodiment.

Figure 4:
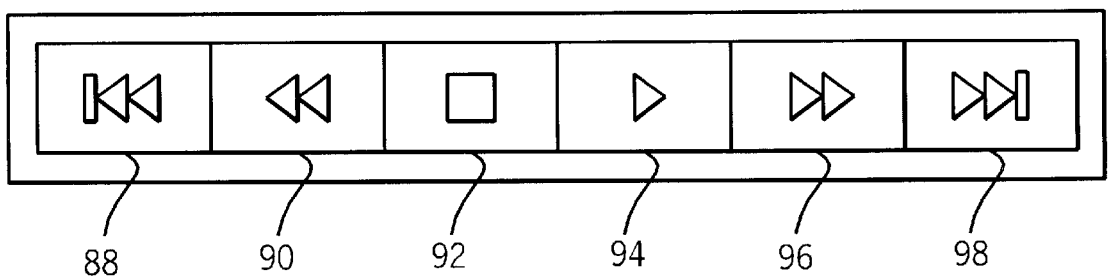
FIG. 4 is a simplified diagram of user controls for paging through historical data presented in a form such as that illustrated in FIG. 2; and, FIG. 5 is a block diagram illustrating exemplary control logic for continuously monitoring fetal status and for transmitting the status data to a remote location upon demand.

Certain display configuration settings may be stored and fixed, while other settings may be user-manipulated. In the data flow of FIG. 3, chart speed, paper and layout orientation, dot pitch, and similar parameters used to define the emulated strip chart presentation are predefined, as represented by reference numeral 80. Additional inputs may be user-controlled, such as scroll controls as indicated at reference numeral 82, and as discussed below. Such scroll controls may permit the user to view a desired section of the data presentation, obviating the need to present all stored presentation data in one view. Based upon the stored data, the display configuration parameters 80, and the user-input commands of 82, the applet configures the strip chart presentation shown in FIG. 2 as indicated at numeral 84. The combined information is then converted to a display as indication at reference numeral 86. In a presently preferred embodiment, all display definition and updating is performed to an off-screen image which is subsequently copied to the screen to avoid flicker when scrolling or updating.

Where data is presented in a form capable of being scrolled, as described above, various types of scroll controls may be provided. For example, FIG. 4 illustrates one type of scroll control interface which may be displayed in one of menus 50 (see FIG. 2) as virtual buttons or similar command devices. The scroll control may thus include such commands as fast reverse to start 88, fast reverse 90, stop 92, forward 94, fast forward 96, and fast forward to stop 98. Other user input devices and interfaces may, of course, be provided. For example, in certain data presentations, more informative information may be provided in various "zoom-in" and "zoom-out" commands.

It should be noted that the various presentations provided by the present technique may be requested, transmitted, and displayed in the client-server environment, without the need for specialized software. Thus, the user may access the data and maintain continuous monitoring of the data remotely, while continuing to perform other operations in the same browser in which the data is accessed and displayed, as well as other applications operating on station 14. To the extent that software updates are necessary at the server side, such as within institution 12, such improvements or enhancements may be implemented without the need for other compatible or similar improvements on the client side. Where various compatibility issues may arise, these are preferably limited to updates in the general purpose browser or applets. Compatibility and efficiency in data access, transfer and display are thereby significantly enhanced.

Figure 5:
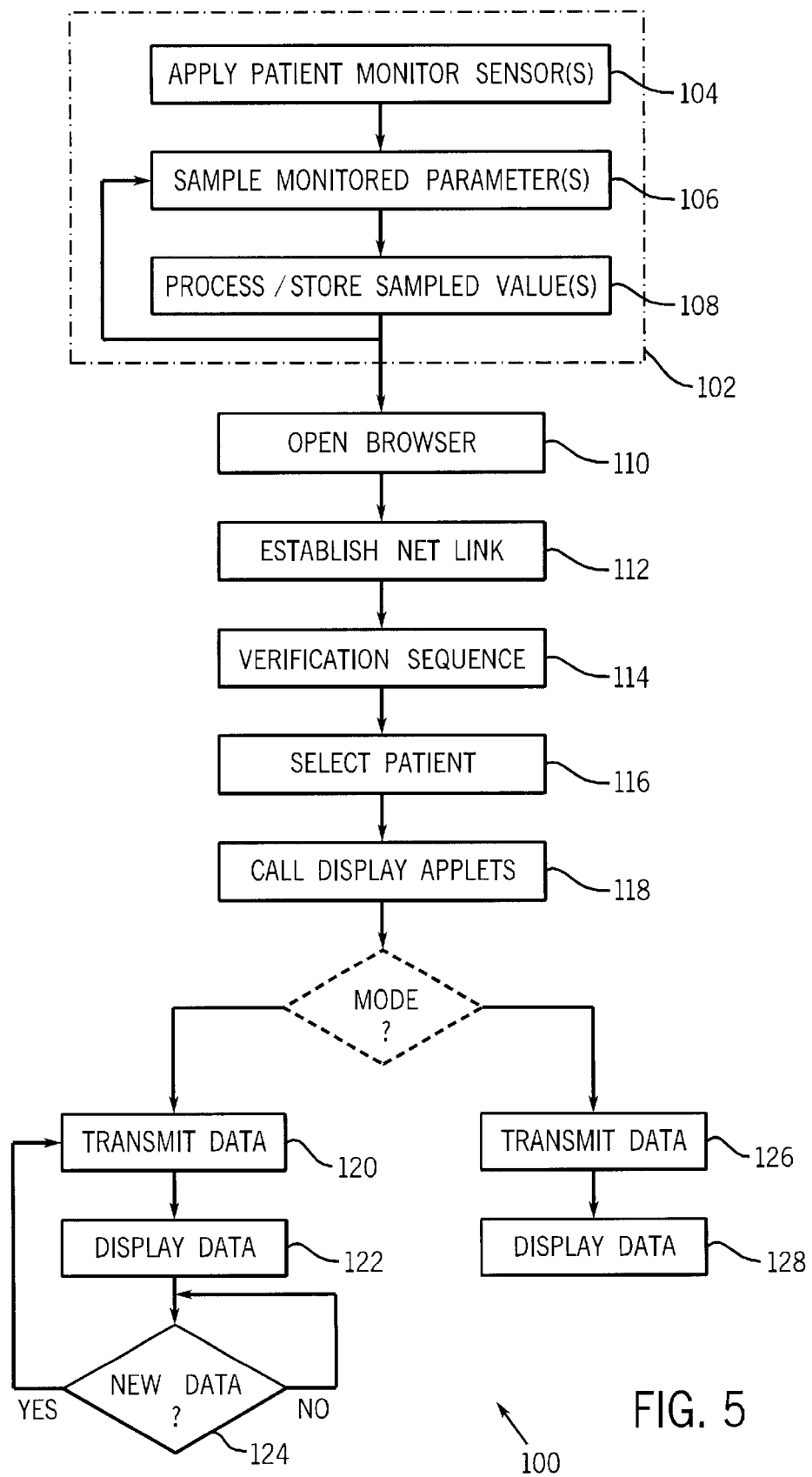

FIG. 5 represents steps in exemplary control logic executed by system 10 for the continuous or periodically sampled monitoring functions and remote data transfer described above. The logic summarized in FIG. 5 may be implemented by any suitable computer code well within the capabilities of skilled programmers. The control logic, designated by reference numeral 100, includes a patient monitoring cycle as designated generally at reference numeral 102. This cycle may include a wide range of monitoring and signal processing steps, but will generally include the overall steps illustrated in FIG. 5. Specifically, the monitoring routine begins with application of a patient monitor sensor or sensors as indicated at step 104. As described above, such sensors may include any suitable transducers or similar devices, such as heartbeat monitors, ultrasonic microphones, pressure sensors, chemical analysis sensors, and so forth. Output from the sensors is sampled as indicated at step 106 at a sampling rate which conforms to the type of parameters being sensed.

As indicated at step 108, such sensed parameter data is then processed and sampled values are stored. This processing may include any suitable filtering, scaling, dynamic range adjustment, analysis, and so forth. For example, in the case of fetal heartbeat monitoring, output from a heart beat sensor is analyzed to determine the likely time at which a specific reference point in the cardiac cycle occurs. Based upon the time between such cycles, a heartbeat rate may be calculated periodically and stored for presentation.

The sequence of sensing, sampling, processing and storing steps summarized above are performed on a repeated basis as needed for monitoring the patient status conditions. As noted above, the steps may be performed in various orders and at various sampling frequencies. Moreover, while the monitoring and sampling steps will generally be performed locally to the patient being monitored, the steps of processing and storing the sampled status values may be performed at any location within the medical institution, or even remote to the institution. Similarly, shared system components may be configured to receive and monitor data on a number of patients with various conditions and needs, with data being stored in a central data management system, where desired.

Step 110 in FIG. 5 is performed at the remote monitoring station described above. In general, at step 110, the user will access general purpose data presentation software and any support software needed for configuring the presentation data. In a presently preferred embodiment, a general purpose web browser is opened at step 110, with support applets being opened only as needed by the data presentation transferred in a subsequent process step. At step 112, a network link is established between the remote monitoring station and the medical institution. Again, this network link may have any suitable configuration, such as an Internet connection via conventional telephony lines, T1 lines, ISDN connections, digital subscriber line connections, fiber optic cable, radio telemetry, and so forth. The establishment of the network link permits two-way communication of commands and data between the remote monitoring station and the medical facility. Thus, step 112 will generally include any necessary URL identification, dial up, hand shake, and similar network communications steps.

At step 114, a verification sequence is preferably performed. Because the data transmitted by the present technique may include sensitive health care information, a verification sequence executed at step 114 will preferably include identification of the requesting user, accompanied by checks of confidential passwords, user subscriptions, and any other information useful to maintain secured access. Cross-referenced information needed for the verification sequence at step 114 may be stored at the medical facility for reference upon demand. At step 116, once logged in via the network link, the user selects a patient for remote monitoring.

At step 118, with the network link established and the user in communication with the medical facility server and patient selection, data is transferred for configuration of the display at the remote monitoring station as described above. In particular, support software, such as Java applets, may be called at step 118 to format the data display. Where desired, certain of these applications may be stored at the medical facility, or elsewhere in memory or network sites accessible by the user. Moreover, where necessary support routines are absent from the user's computer, and these are detected by the server, the user may be prompted to acquire or download such support software.

The transfer of monitored parameter data is preferably carried out in real time, with both updated and historical data being accessed and transferred for display. Alternatively, modes may be defined for the transfer of data, with real time and historical modes being defined separately, as indicated by the decision block shown in broken lines in FIG. 5. Such modes may be user selected, where provided.

In the illustrated embodiment, a real time mode is used for data transmission, as indicated at step 120. As summarized above, the data may be transmitted for a predetermined historical time period, such as the most recent four hours, and updated continuously. However, any suitable time period may be employed, with the desired time generally being selected in accordance with the type of condition being monitored, the quantity of historical data available, and the importance of historical data in evaluating the patient's condition. At step 122 this data is formatted and displayed as summarized above, again calling upon specialized support software or routines where needed. At step 124 the system determines whether new data has become available through the process steps summarized above and indicated generally in FIG. 5 by reference numeral 102. The updating inquiry at step 124 may be automatic and performed at the server side of system 10. Alternatively, the monitoring station may be automatically or manually prompted to obtain updated data at step 124. When such data becomes available, the updated data is transmitted at step 120 and redisplayed as indicated above at step 122. To promote the rapid and efficient transfer and display of updated data, only newly available data is transmitted and inserted upon each cycle through step 120 and 122.

Additional information and data may be transmitted and displayed for the user where desired. For example, in a presently preferred configuration, information such as bed names, time and date, date of last vaginal exam, vital signs (including blood pressure, and maternal heart rate), membrane status, and patient name, may also be transmitted. Help files and similar user aids be similarly be provided for navigation, command, and interpretation of the data. In the case of fetal heartbeat rate monitoring, several traces may be provided depending upon the number of fetuses being monitored, with separate traces being indicated by separate colors or patterns to provide an indication of separate heartbeats. Similarly, where several patients are contemporaneously monitored in a single institution, or even between institutions, an attending physician may be allowed to monitor data for several such patients by navigation through a menu of occupied beds, patient names, attending physicians, and similar variables.

If provided, in a historical mode illustrated in FIG. 5, data is accessed and transmitted at step 126 in a manner similar to that described with respect to step 120. Again, this data is formatted and displayed as indicated at step 128. However, if automatic updating is not desired or necessary, the transmission after step 128 terminates and the system awaits further commands from the user.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A system for remotely monitoring a patient status parameter, the system comprising:

a fetal monitor including a sensor for detecting a patient status parameter and for producing a parameter signal representative thereof;

a server-side controller coupled to the sensor for receiving the parameter signal and for incorporating the parameter signal into a client viewable presentation; and a client-side controller including a general purpose browser configured to be coupled to the server-side controller via a network connection to receive data from the server-side controller and for displaying the client viewable presentation.

2. The system of claim 1, wherein the client viewable presentation includes at least one viewable page formatted via a markup language.

3. The system of claim 1, wherein the client viewable presentation includes a graphical representation of the patient status parameter.

4. The system of claim 1, wherein the sensor is configured to detect a heartbeat of a fetus.

5. The system of claim 1, wherein the client viewable presentation includes historical presentation of the patient status parameter viewable via the browser by user selection of a time period range.

6. The system of claim 1, comprising a plurality of sensors coupled to the server-side controller for detecting a plurality of patient status parameters, including at least one fetal monitor parameter, and wherein the client viewable presentation includes a display of data representative of the plurality of patient status parameters.

7. The system of claim 1, wherein the client-side controller is configured to be coupled to the server-side controller via an open network.

* * * * *